United States Patent [19]
Dürschmidt et al.

[11] Patent Number: 5,018,348
[45] Date of Patent: May 28, 1991

[54] METHOD FOR DETECTING THE CONDITION OF CATALYTIC CONVERTERS

[75] Inventors: Ferry Dürschmidt, Friolzheim; Harmut Kolb, Ludwigsburg; Wolfgang Strauss, Denkendorf; Hartmut Weckenmann, Stuttgart, all of Fed. Rep. of Germany

[73] Assignee: Daimler-Benz AG, Fed. Rep. of Germany

[21] Appl. No.: 442,316

[22] Filed: Nov. 28, 1989

[30] Foreign Application Priority Data

Dec. 10, 1988 [DE] Fed. Rep. of Germany ....... 3841685

[51] Int. Cl.$^5$ .............................................. F01N 3/18
[52] U.S. Cl. ........................................ 60/274; 60/276; 60/277
[58] Field of Search ........................ 60/274, 277, 276

[56] References Cited

U.S. PATENT DOCUMENTS

| | | | |
|---|---|---|---|
| 4,622,809 | 11/1986 | Abthoff | 60/276 |
| 4,707,984 | 11/1987 | Katsuno et al. | |
| 4,707,985 | 11/1987 | Nagai et al. | |
| 4,720,973 | 1/1988 | Katsuno | |
| 4,739,614 | 4/1988 | Katsuno | 60/276 |
| 4,761,950 | 8/1988 | Nagai et al. | |

FOREIGN PATENT DOCUMENTS 2758835 7/1979 Fed. Rep. of Germany.
3224347 8/1983 Fed. Rep. of Germany.

*Primary Examiner*—Douglas Hart
*Attorney, Agent, or Firm*—Evenson, Wands, Edwards, Lenahan & McKeown

[57] ABSTRACT

An internal combustion engine has a catalytic converter in its exhaust gas path. In the catalytic converter, two exhaust gas emission measuring probes are provided spatially separated from one another. The phase shift between the output signals of these two measuring probes is used as a measure of the aging of the catalytic converter.

5 Claims, 1 Drawing Sheet

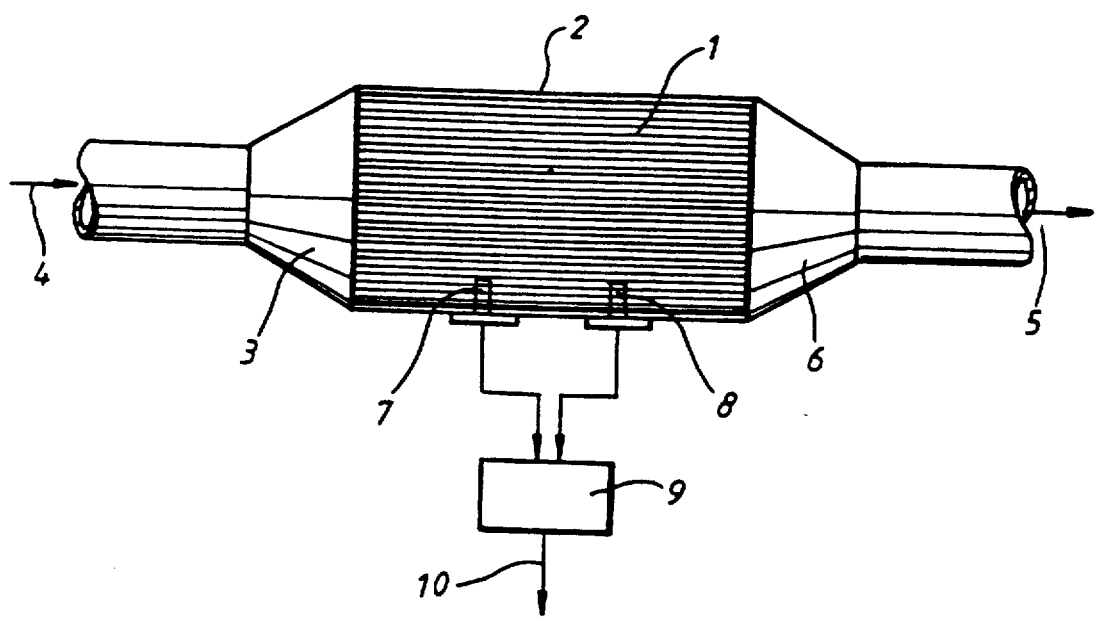

METHOD FOR DETECTING THE CONDITION OF CATALYTIC CONVERTERS

BACKGROUND AND SUMMARY OF THE INVENTION

The invention relates to a method and device for detecting an operational condition of catalytic converters.

For internal combustion engines having a catalytic converter and exhaust gas emission measuring probes for post-treatment of exhaust gas, German Published, Unexamined Patent Application 3,224,347 disclosed the analysis of a partial oxygen pressure with the aid of these probes and the control, in dependence thereupon, of a fuel/air ratio of a fuel mixture fed to the internal combustion engine to an almost stochiometric value. For this analysis, the known behavior of an oxygen probe is utilized, i.e. that of changing its output voltage in dependence on the presence of oxygen in the exhaust gas. In this connection, a very steep change in the output voltage within a narrow range around the stochiometric ratio ($\lambda = 1$) is characteristic of the oxygen probe.

If, during the comparison of the signal emitted by the probe with a predetermined threshold value, a low partial oxygen pressure is detected, that is to say a rich mixture is detected, the composition of the fuel mixture is uniformly made leaner with the aid of an integrator contained in a control device. Conversely, the fuel/air ratio is uniformly enriched when a high partial pressure is detected, that is to say a lean mixture is detected. If a change between the two ranges, i.e. rich and lean, is detected in the fuel/air ratio, the fuel mixture composition is changed by a constant amount. This control behavior described above is produced, for example, via a proportional integral (PI) controller.

In the control method discussed above, it is possible to adapt the control system to various operating conditions of the internal combustion engine in that, for example, the speed of integration of the PI control is selected in dependence on load and rotational speed of the internal combustion engine. It is also possible to select the control parameters in dependence on the operating time of the catalytic converter in order to compensate for the decreasing conversion rate of the catalytic converted with increasing operating time. The operating time can be detected via the operating hours and via the distance travelled. In both possibilities, however, the actual state of activity of the catalytic converter is not detected since this is additionally influenced by various load/speed collectives.

Thus, it is an object of the present invention to detect an actual state of operational activity of a catalytic converter and to provide running time dependent interventions for a control arrangement of an internal combustion engine.

According to preferred embodiments of the invention, this object and other objects are achieved by providing, at the catalytic converter volume, two probes for detecting the exhaust gas composition, the probes being spatially separated from one another. These probes are usually oxygen probes with the aid of which a transition from a rich to a lean fuel/air ratio and conversely is detected. The spatially separated arrangement of the two probes results in a time delay between the two probe signals during the exhaust gas emission measurement. This time delay that is to say the phase shift between the two probe signals, is a measure of the activity of the catalytic converter and thus of its state of aging which influences the conversion rate of the catalytic converter. The result of the measurement of the phase shift is used as additional input parameter for a conventional control system and thus enables running time dependent interventions to be carried out.

Other objects, advantages and novel features of the present invention will become apparent from the following detailed description of the invention when considered in conjunction with the accompanying drawings.

BRIEF DESCRIPTION OF THE DRAWING

The single drawing FIGURE of the application illustrates one embodiment of the present invention.

DETAILED DESCRIPTION OF THE DRAWING

The single FIGURE diagrammatically shows a catalytic converter 1, which is arranged in a housing 2. At an upstream end 3, exhaust gas 4 flows in the direction of the arrow coming from an internal combustion engine, not shown here, into the catalytic converter 1. After passing through the entire catalytic converter volume, the exhaust gas 5, which is now cleaned, leaves the catalytic converter 1 at a downstream end 6 and from there passes in the direction of the arrow into an exhaust system, also not shown here.

When passing through the catalytic converter 1, the exhaust gas flows past two oxygen probes 7 and 8 which have, in familiar manner, an abrupt change in voltage when a change of the fuel/air ratio from rich to lean or conversely is detected. Due to the spatially separated arrangement of these two probes 7 and 8, such a change in the fuel/air ratio is mandatorially detected later by the downstream probe 8 than by the upstream probe 7.

This arrangement results in a time delay in the signal output of probe 8 compared with probe 7, which is evaluated as a phase shift signal in an evaluating unit 9. The amount of phase shift is a measure of the state of activity and thus also of the aging of the catalytic converter 1. The result 10 of the phase shift measurement can then be used as an input parameter for running time dependent interventions into the control, not shown here, of the fuel/air ratio and thus aging-related deteriorations in the degree of conversion of the catalytic converter 1 can be compensated.

The method according to preferred embodiments of the invention is found to be particularly advantageous in interaction with a control method in which a periodic oscillation is impressed on the fuel/air ratio. The control frequency of the system can be increased via an increase in the frequency of this impressed oscillation in dependence on the phase shift signal 10 and as already shown above, aging-related deteriorations in the degree of conversion of the catalytic converter 1 can be compensated. In this arrangement, the use of a sinusoidally impressed oscillation is particularly suitable since the sinewave shape is not distorted but only the amplitude of this oscillation is attenuated by the transfer function of the catalytic converter 1, which represents a delay section and exhibits low-pass filter behavior. This results in a particularly simple evaluation of the measurement results at probes 7 and 8.

In an advantageous embodiment, an intermediately located portion of the catalytic converter volume located between the two probes 7 and 8 is about 10% to 30% of the total catalytic converter volume. Although the detection of aging is in principle improved by a greater intermediately located portion of the catalytic converter volume, this layer spacing degrades the detectability of the signals and their association with one another by the same amount due to the rounding of the signals due to the low-pass filter characteristic of a catalytic converter.

The information on the state of aging of the catalytic converter 1 becomes particularly advantageous for the case where the catalytic converter volume, located between probes 7 and 8, is the front section, that is to say the upstream, thermally highly loaded end of the catalytic converter 1.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. A method for detecting the operational condition of a catalytic converter having a volume in an exhaust gas path of an internal combustion engine comprising the steps of:
   arranging an upstream gas emission probe and a downstream exhaust gas emission probe in the exhaust gas path on either side of an intermediately located portion of the volume of the catalytic converter;
   detecting a phase shift between output signals of the upstream and downstream gas emission probes; and
   evaluating the phase shift between the output signals as a measure of a state of aging of the catalytic converter.

2. A method according to claim 1, further comprising the steps of:
   controlling a fuel/air mixture supplied to the internal combustion engine to a stoichiometric value; and
   modifying the control step in accordance with the state of aging of the catalytic coverter.

3. A device for detecting the operational condition of a catalytic converter having a volume in an exhaust gas path of an internal combustion engine comprising:
   an upstream gas emission probe and a downstream exhaust gas emission probe in the exhaust gas path on either side of an intermediately located portion of the volume of the catalytic converter;
   detecting means for detecting a phase shift between output signals of the upstream and downstream probes; and
   evaluating means for evaluating the phase shift between the signals as a measure of a state of aging of the catalytic converter.

4. A device according to claim 3, wherein the intermediately located portion of the volume of the catalytic converter is about 10% to 30% of the volume.

5. A device according to claim 4, wherein the intermediately located portion of the volume of the catalytic converter is located at an upstream end of the catalytic converter.

* * * * *